United States Patent
Shats

(10) Patent No.: US 10,743,746 B2
(45) Date of Patent: Aug. 18, 2020

(54) ENDOSCOPIC DEVICE

(71) Applicant: Daniel Shats, Wheeling, WV (US)

(72) Inventor: Daniel Shats, Wheeling, WV (US)

( * ) Notice: Subject to any disclaimer, the term of this patent is extended or adjusted under 35 U.S.C. 154(b) by 307 days.

(21) Appl. No.: 14/299,697

(22) Filed: Jun. 9, 2014

(65) Prior Publication Data

US 2015/0351612 A1    Dec. 10, 2015

(51) Int. Cl.
| | | |
|---|---|---|
| *A61B 10/04* | (2006.01) | |
| *A61B 1/00* | (2006.01) | |
| *A61B 1/018* | (2006.01) | |
| *A61B 1/015* | (2006.01) | |
| *A61B 18/14* | (2006.01) | |
| *A61B 10/02* | (2006.01) | |
| A61B 18/00 | (2006.01) | |
| A61B 17/00 | (2006.01) | |

(52) U.S. Cl.
CPC ...... *A61B 1/00094* (2013.01); *A61B 1/00082* (2013.01); *A61B 1/015* (2013.01); *A61B 1/018* (2013.01); *A61B 10/0283* (2013.01); *A61B 10/04* (2013.01); *A61B 18/1492* (2013.01); *A61B 2017/0034* (2013.01); *A61B 2018/00607* (2013.01); *A61B 2018/00982* (2013.01); *A61B 2018/1465* (2013.01)

(58) Field of Classification Search
CPC ............ A61B 1/00082; A61B 10/0283; A61B 1/00094; A61B 10/04; A61B 18/082; A61B 18/085; A61B 18/14; A61B 1/015; A61B 1/018; A61B 1/0125; A61B 18/1492; A61B 18/1477; A61B 2017/0034
See application file for complete search history.

(56) References Cited

U.S. PATENT DOCUMENTS

| | | | |
|---|---|---|---|
| 4,791,937 A | | 12/1988 | Wang |
| 5,336,172 A | * | 8/1994 | Bales .................. A61B 17/3203<br>604/158 |
| 8,317,786 B2 | * | 11/2012 | Dahla ................ A61B 18/1402<br>604/119 |
| 2004/0243023 A1 | | 12/2004 | Grigoryants et al. |
| 2006/0235433 A1 | * | 10/2006 | Secrest ............ A61B 17/32056<br>606/114 |

(Continued)

FOREIGN PATENT DOCUMENTS

| | | |
|---|---|---|
| JP | 2006334149 A | 12/2006 |
| WO | WO-2015191341 A1 | 12/2015 |

OTHER PUBLICATIONS

"International Application Serial No. PCT/US2015/033927, International Search Report dated Sep. 21, 2015", 3 pgs.

(Continued)

*Primary Examiner* — Devin B Henson
*Assistant Examiner* — Huong Q Nguyen
(74) *Attorney, Agent, or Firm* — William F. Lang, IV; Lang Patent Law LLC

(57) ABSTRACT

A tool for an endoscope comprises an elongated shaft including a proximal end and a distal end, wherein the elongated shaft comprises a tubular member with an interior channel extending from the distal end toward the proximal end and a one or more perforations in the tubular member that are spaced from the distal end, the one or more perforations providing fluid communication between an exterior of the elongated shaft and the interior channel.

21 Claims, 3 Drawing Sheets

(56) References Cited

U.S. PATENT DOCUMENTS

2007/0179341 A1* 8/2007 Okada ................ A61B 1/00068
                                                      600/156
2009/0182194 A1* 7/2009 Wood ................... A61B 1/0008
                                                      600/106
2012/0277742 A1* 11/2012 Laufer ................... A61B 17/30
                                                      606/45

OTHER PUBLICATIONS

"International Application Serial No. PCT/US2015/033927, Written Opinion dated Sep. 21, 2015", 5 pgs.

* cited by examiner

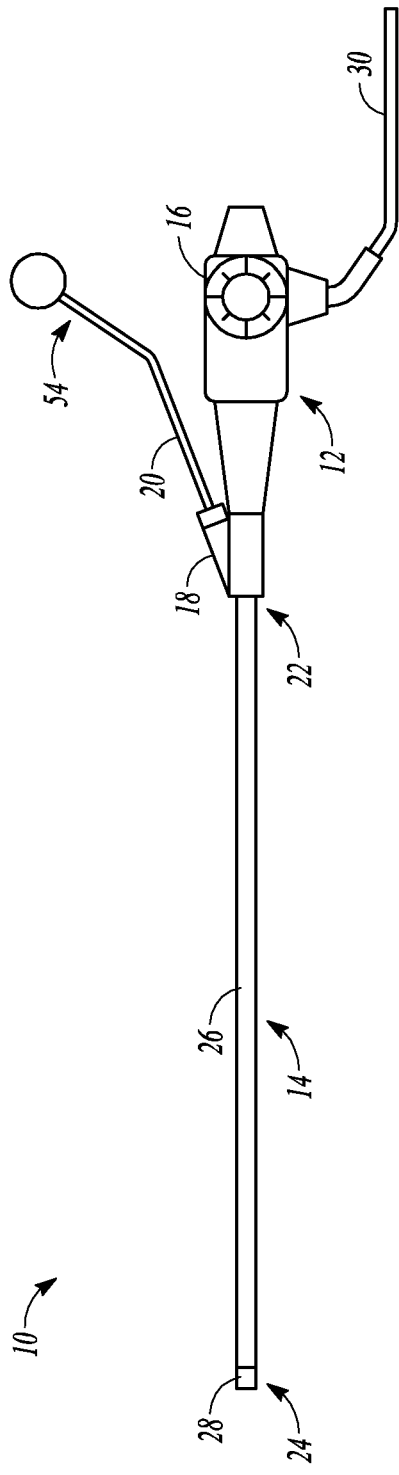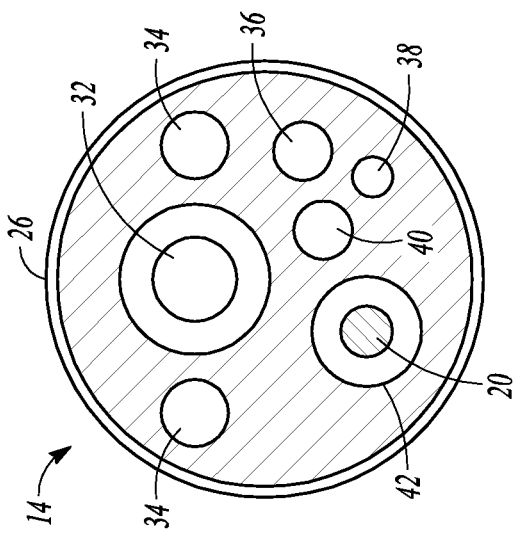

ENDOSCOPIC DEVICE

BACKGROUND

An endoscope is an instrument that can be used for examination and surgical modification within cavities of the body. For example, an endoscope can be configured to be inserted into the intestinal tract of a patient, such as a colonoscope that is configured for examination of the colon. The endoscope can include a digital imaging device at a distal end of the endoscope, such as a charge coupled device (CCD) light sensor. Other functionality can be provided to the endoscope, such as the ability to introduce water or air into a body cavity or to perform suction in order to remove fluids or material through the working channel of the endoscope.

An endoscope can also be configured for biopsy of tissue from the portion of the body that it is configured to examine. For example, a colonoscope can be configured for the removal of tissue from the colon, such as colon polyps that are found during a colonoscopy. A common method for removing polyps from the colon is the snare polypectomy technique, which uses a wire with a lasso-like loop that can be placed around the polyp. The loop can be tightened around the polyp and optionally can be energized to cut off and, if necessary, cauterize the location of the polyp. The polyp can then be collected through the working channel of the endoscope for later inspection.

While the snare polypectomy technique can be advantageous due to its simplicity, snares are not perfect in capturing polyps. A certain percentage of polyps can be lost within the body cavity, which can lead to difficulty in locating and retrieving the lost polyp.

SUMMARY

The present disclosure describes a tool for use in an endoscope that is configured for more efficient and reliable capture of tissue, such as polyps, or other objects during an endoscopic procedure. The tool can provide for the use of an endoscope's suction capability and can transfer at least a portion of the suction force into an interior channel of the tool so that the suction force can be used to capture tissue or other materials and help retain the captured material for removal from the patient.

In an example, a tool for an endoscope can include an elongated shaft including a proximal end and a distal end, wherein the elongated shaft comprises a tubular member with an interior channel extending from the distal end to the proximal end, and one or more perforations in the tubular member that are spaced from the distal end, the one or more perforations providing fluid communication between the exterior of the elongated shaft and the interior channel.

In another example, an endoscope comprises an operating unit comprising one or more controls for operating the endoscope, an insertion member coupled to the operating unit at a proximal end and extending to a distal end, the insertion member comprising a working channel extending from the proximal end to the distal end through an interior of the insertion member, wherein the operating unit is configured to provide suction within the working channel and a tool insertable into the working channel, the tool comprising an elongated shaft extendable through the working channel, the elongated shaft comprising a shaft proximal end and a shaft distal end, the elongated shaft comprising a tubular member with an interior channel extending from the shaft distal end toward the shaft proximal end, and a one or more perforations in the tubular member spaced from the shaft distal end, the one or more perforations providing fluid communication between the working channel of the insertion member and the interior channel of the elongated shaft such that the suction applied to the working channel can be transferred to the interior channel of the tool.

These and other examples and features of the present systems and methods will be set forth in part in the following Detailed Description. This Summary is intended to provide an overview of the present subject matter, and is not intended to provide an exclusive or exhaustive explanation. The Detailed Description below is included to provide further information about the present systems and methods.

BRIEF DESCRIPTION OF THE FIGURES

FIG. 1 is a side view of an example endoscope.

FIG. 2 is a cross-sectional view of the example endoscope taken along line 2-2 in FIG. 1.

DETAILED DESCRIPTION

Figure 3:
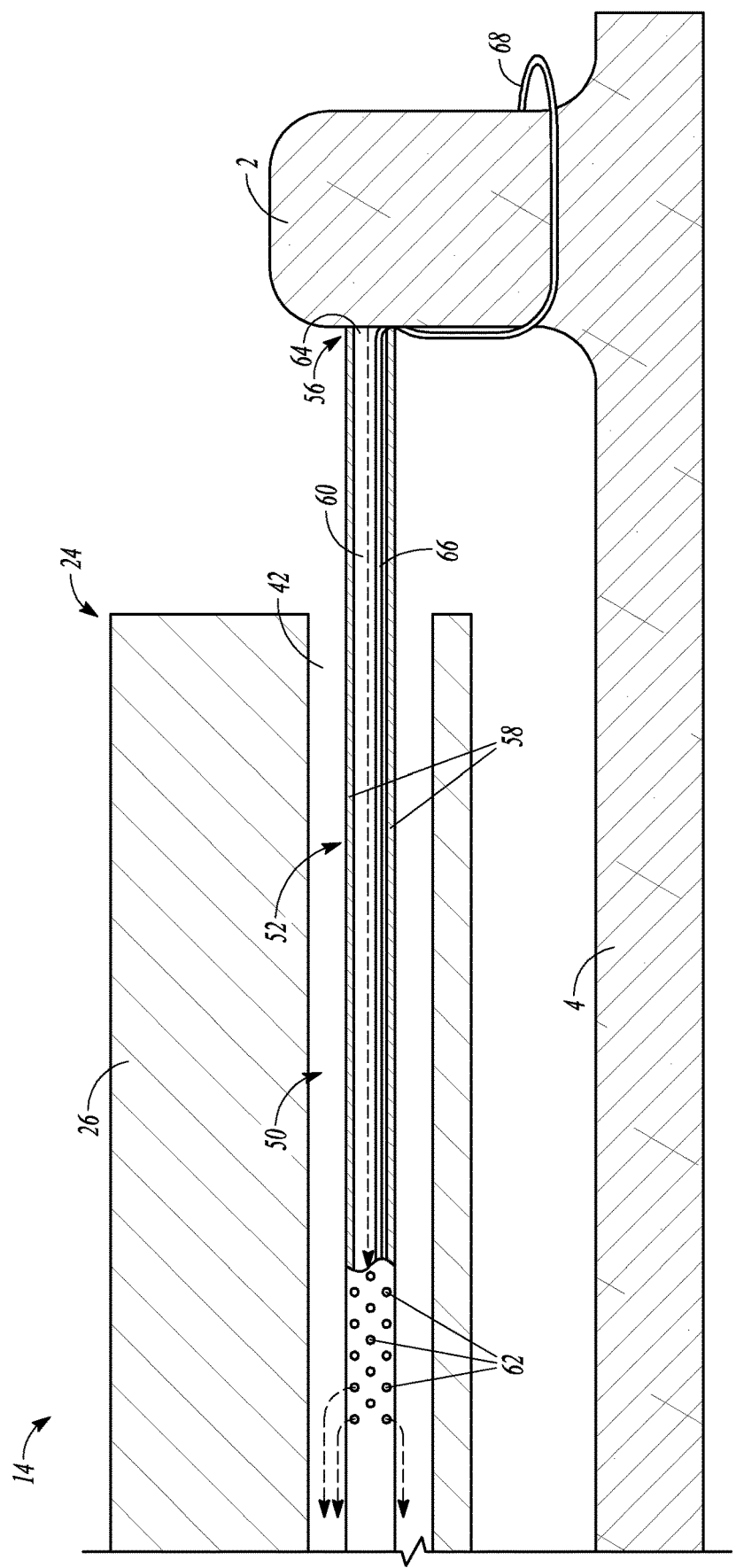
FIG. 3 is a cross-sectional side view of a distal end of an example tool for use within the example endoscope.

In the following Detailed Description, reference is made to the accompanying drawings that form a part hereof. The drawings show, by way of illustration, specific examples in which a tool can be used with an endoscope. These examples are described in sufficient detail to enable those skilled in the art to practice, and it is to be understood that other embodiments can be utilized and that structural changes can be made without departing from the scope of the present disclosure. Therefore, the following Detailed Description is not to be taken in a limiting sense, and the scope of the present disclosure is defined by the appended claims and their equivalents.

This disclosure describes an endoscope and a tool that can be used therewith. The tool can be configured to use the existing suction being applied to the working channel of the endoscope and to transfer the applied suction to an internal channel within the tool so that an object, for example tissue such as a polyp, can be captured using the transferred suction. The tool and endoscope can provide for better capture of objects with less likelihood of the object becoming lost in the body cavity.

FIG. 1 is an overall view of an example endoscope 10 that can be used for the examination of a cavity within a patient. For example, the endoscope 10 can be a colonoscope used for examining the colon of a human patient. The endoscope 10 can include an operating unit 12 and an insertion member 14 coupled to the operating unit 12. The operating unit 12 can include one or more controls 16 that allow a user, such as a surgeon, to operate the endoscope 10. A tool inlet channel 18 can be included on the operating unit 12, which can provide for an inlet through which a tool 20, such as a biopsy tool 20, can be inserted so that the tool 20 will be inserted into the insertion member 14, as described in more detail below.

The insertion member 14 can include a proximal end 22 coupled to the operating unit 12, a distal tip 24, and an elongated shaft 26 extending from the proximal end 22 to the distal tip 24. A digital imaging device 28 can be mounted at the distal tip 24 of the insertion member 14 to capture images or video of the view at the distal tip 24 (e.g., from within the patient cavity being examined). In an example, the digital imaging device 28 can comprise a charge coupled device (CCD) light sensor.

In an example, a portion of the insertion member 14 can be deflectable for better maneuverability of the insertion member 14 through the patient cavity. For example, the elongated shaft 26 can be configured so that the distal tip 24 can be deflected in one or more directions for maneuvering through tight orifices or sharp bends in the patient's body cavity. Deflection of the distal tip 24 or other portions of the insertion member 14 can also be employed to allow the user performing the examination a better angle of view toward a particular portion of the body cavity. Deflection of the distal tip 24 or any other portion of the insertion member 14 can be controlled by the controls 16 on the operating unit 12.

An umbilical cable 30 can be coupled to the operating unit 12, for example to provide one or more of an electrical connection to a power source (not shown), a fluid communication to a suction source (not shown) to provide suction to the insertion member 14, an air source (not shown) for pumping air into and through the insertion member 14 (e.g., for expanding the cavity with air to provide for a better view of the cavity), or a water source (not shown) for pumping water into and through the insertion member 14, e.g., to clear an obstruction away from the distal tip of the insertion member 14.

FIG. 2 shows an end view of the insertion member 14 taken at the distal tip 24. As shown in FIG. 2, the elongated shaft 26 of the insertion member 14 can include one or more structures that can provide useful functionality to the endoscope 10. The digital imaging device 28 can include a lens 32 that can have a view looking out from the distal tip 24 (e.g., out from the page in FIG. 2). The insertion member 14 can include one or more lighting structures, such as one or more light guides 34 that can provide light at the distal tip 24 so that the environment within the body cavity can be captured by the digital imaging device 28. One or more water tubes 36, 38 can pass through the elongated shaft 26 to feed water to the distal tip 24. In an example, a first water tube 36 can provide water at a low rate, e.g., to drip or flow water over the distal tip 24, for example to clean off the lens 32. A second water tube 38 can provide water at a higher rate, e.g., to provide a jet of water that can remove objects or materials that are obstructing the view of the digital imaging device 28. The insertion member 14 can also include an air tube 40 to supply air out of the distal tip 24. In the case of the endoscope 10 being used for a colonoscopy, for example, air fed through the air tube 40 can expand the colon, essentially inflating it, to make it easier for crevices within the colon to be viewable by the digital imaging device 28.

The insertion member 14 can also include a working channel 42, also referred to as an instrument channel 42 or a tool channel 42. The working channel 42 can provide a pathway for the tool 20 to be inserted through the elongated shaft 26 so that a distal end of the tool 20 can access the distal tip 24 of the insertion member 14, in some cases allowing the distal end of the tool 20 to be extended out beyond the distal tip 24. For example, if a particular portion of tissue is to be examined, such as a polyp, the tool 20 can be extended out of the insertion member 14 and be put in contact with the tissue (as described in more detail below).

In an example, the endoscope 10 can be any standard endoscope that is currently on the market. In other words, the endoscope 10 need not be specially designed for the tool 20 described herein (other than that the tool 20 must be able to fit through the tool inlet channel 18 and the working channel 42). Rather, the tool 20 can be designed to use the features of endoscopes that exist in many endoscopes sold on the market. Most notably, as described in more detail below, the tool 20 of the present disclosure can provide for suction-based capturing of material, for example capturing of tissue, such as a polyp, by using the existing suction capability of the endoscope 10 such that a separate suction source and system are not required.

FIG. 3 shows a side view of an example tool 50 that can be used in an endoscope. The tool 50 can be used, for example, with the endoscope 10 shown in FIG. 1 as the tool 20. The tool 50 can include an elongated shaft 52 which can extend through the working channel 42 of the endoscope 10. The shaft 52 can extend from a shaft proximal end 54 (shown in FIG. 1) to a shaft distal end 56. At least a portion of the shaft 52 that is proximal to the shaft distal end 56 comprises a tubular member 58 with an interior channel 60. The interior channel 60 can extend from the shaft distal end 56 toward the shaft proximal end 54. In an example, the interior channel 60 can extend all the way from the shaft distal end 56 to the shaft proximal end 54, e.g., so that a tool implement can be inserted through the interior channel 60 or tool components can be housed within the interior channel 60, such as a cautery structure that can cut and cauterize the tissue being captured by the tool 50. In an example, one or both of the shaft 52 and the tubular member 58 can have a circular cross-section (i.e., they can form a circular cylinder), as is typical for tools used in medical devices such as endoscopes. However, a circular cross-sectional shape of the shaft 52 and the tubular member 58 is not required, and one or both of the shaft 52 and the tubular member 58 can have other cross-sectional shapes, such as square, rectangular, triangular, ovular, pentagonal, octagonal, or other regularly or irregularly shaped cross-sections.

The tool 50 can be configured to provide for suction-based capture of material such as tissue at the distal end 56 of the elongated shaft 52. The suction-based capture can be enabled by one or more perforations 62 in the tubular member 58 that extend between the interior channel 60 and an exterior of the elongated shaft 52 of the tool 50. The perforations 62 can provide a fluid pathway between the exterior of the elongated shaft 52 and the interior channel 60, e.g., to provide a fluid pathway between the interior channel 60 and the portion of the working channel 42 surrounding the elongated shaft 52 of the tool 50. As described above, the endoscope 10 can supply suction to the working channel 42 (e.g., for removal of material through the working channel 42), which can create a vacuum inside the working channel 42, e.g., through the umbilical cable 30 to a suction source. The perforations 62 can be configured so that the fluid pathway provided by the perforations 62 can transfer at least a portion of the vacuum from the working channel 42 exterior to the elongated shaft 52 of the tool 50 into the interior channel 60 within the shaft 52. The transfer of at least a portion of the vacuum is shown conceptually by the dashed arrows in FIG. 3, which represent the direction of fluid flow when suction force is applied to the working channel 42 and is transferred into the interior channel 60 through the perforations 62. This transfer of the vacuum can produce suction at the distal end 56 of the elongated shaft 52, e.g., through an opening 64 at the distal end 56, without requiring a suction source separate from the suction source that provides suction to the working channel 42.

The perforations 62 can be configured in any way that will provide for sufficient transfer of vacuum from the working channel 42 into the interior channel 60 and thus to the shaft distal end 56. The perforations 62 can be spaced from the shaft distal end 56 and can be positioned at any point along the elongated shaft 52. In some examples, the position of the perforations 62 can be limited to being close enough to the shaft distal end 56 to provide sufficient suction at the shaft distal end 56, but far enough from the shaft distal end 56 that, when the tool 50 is in use, a sufficient number of the perforations 62 will be located in the working channel 42 when suction is applied so that the suction can be transferred from the working channel 42 to the interior channel 60. This can ensure that the perforations 62 are not so close to the shaft distal end 56 that they extend out of the working channel 42 when the tool 50 is extended from the working channel 42 during use. The position of the perforations 62 can depend on how far from the distal tip 24 of the insertion member shaft 26 that the shaft distal end 56 is desired to extend, which can depend on the particular application for which the endoscope 10 is designed. For example, for an endoscope 10 designed for a colonoscopy and polypectomy, it can be desired that the shaft distal end 56 be extendable from the distal tip 24 of the insertion member 14 by at least about 1 centimeter (cm), such as at least about 2 cm, for example at least about 3 cm. In such a case, it can be desirable for the most distal of the perforations 62 to be located at least this distance proximal to the shaft distal end 56, and in some examples at least about 1 cm proximal to the point that the shaft distal end 56 can be desired to extend from the insertion member 14, such as at least about 2 cm. In an example, the most distal perforations 62 can be spaced from the shaft distal end 56 by a distance that can range from about 2 cm to about 10 cm.

Each perforation 62 can have any size or shape that is sufficient to allow for the transfer of suction from the working channel 42 to the interior channel 60. In an example, the size of each perforation 62 may need to be large enough to effectively transfer the vacuum to the interior channel 60, but not so large that the structural integrity of the tubular member 58 is adversely impacted such that the tubular member 58 will not bend or kink when it is being inserted into the working channel 42.

The perforations 62 can form a pattern in the tubular member 58 that is designed for the desired transfer of suction to the interior channel 60. The layout of the pattern of the perforations 62 can depend on the expected suction force or range of suction forces within the working channel 42 and the expected characteristics of that suction (e.g., uniform or non-uniform suction within the working channel 42, etc.). Similarly, the overall area of the tubular member 58 that is populated by the perforations 62 can depend on the expected suction. In an example, the area of the tubular member 58 populated by the perforations 62 can be large enough that the vacuum is sufficiently transferred into the interior channel 60, but not so large that it adversely affects the structural integrity of the tubular member 58. Similarly, the packing of the perforations 62, e.g., the distance between adjacent perforations 62 or the density of perforations 62 on the tubular member 58, can be sufficient for the vacuum to be transferred into the interior channel 60, but not so densely packed that it adversely affects the structural integrity of the tubular member 58.

As shown in FIG. 3, when the suction force is transferred from the working channel 42 to the interior channel 60, an object can be secured to the shaft distal end 56 via suction when suction is being applied to the working channel 42. For example, a portion of the patient's tissue, such as a polyp 2 within the patient's colon 4, can be secured to the shaft distal end 56 via suction when suction is being supplied to the working channel 42. This can allow for examination or removal of the object, such as examination or removal of a sample of a tissue, e.g. the polyp 2, to be removed from the patient for subsequent analysis.

The tool 50 can also include a cutting or cauterizing structure 66 that can provide for cutting or cauterizing, or both, of the tissue sample. For example, if the endoscope 10 is to be used for a colonoscopy, and the tool 50 is configured for removal of polyps 2 within the colon 4, the cutting or cauterizing structure 66 can be a structure that can be extended from the tool shaft 52, such as a cautery knife that can be inserted through the interior channel 60 of the tool 50 or through the working channel 42 of the insertion member 14. In an example, shown in FIG. 3, the cutting or cauterizing structure 66 can be in the form of a wire loop 68 that is placed around the polyp 2, similar to a typical wire polypectomy snare. The difference between the wire loop 68 of the cutting or cauterizing structure 66 shown in FIG. 3 and a more typical wire polypectomy snare is the fact that the wire loop 68 need not be designed to capture or secure the polyp 2 after resection of the polyp 2 from the colon 4. The suction supplied to the shaft distal end 56 via the interior channel 60 through the perforations 62 can capture and secure the polyp 2 to the tool 50.

In an example, a method of removing a tissue sample can include placing the wire loop 68 around the tissue, e.g., the polyp 2. Next, the wire loop 68 can be tightened around the tissue, which can be done by operating a handle at the proximal end of the tool 50. Next, suction can be applied to the working channel 42, such as by engaging a suction control of the endoscope 10. The suction can create a vacuum in the working channel 42 that can be transferred to the interior channel 60 of the tool 50 through the perforations 62, as described above. The vacuum in the interior channel 60 can cause the polyp 2 to be secured to the shaft distal end 56. Next, the polyp 2 can be cut by the wire loop 68, such as by further tightening the wire loop 68 so that it cuts into and through the polyp 2, or by energizing the wire loop 68 to cut the polyp 2 and cauterize the location where the polyp 2 is excised. After cutting, the polyp 2 can continue to be held at the shaft distal end 56 by the vacuum being transferred from the working channel 42 into the interior channel 60 through the perforations 62. The shaft 52 can be withdrawn from the working channel 42. While the shaft 52 is being withdrawn, the suction can continue to be applied to the working channel 42 so that the shaft 52 can bring the polyp 2 into the working channel 42, because the polyp 2 is being held by the vacuum at the shaft distal end 56.

The polyp 2 (or any other object that has been captured by the vacuum at the shaft distal end 56) can then be released from the shaft distal end 56. The release of the polyp 2 can occur in several ways. For example, once the shaft 52 is withdrawn far enough that the perforations 62 are withdrawn from the inlet of the endoscope 10 at the tool inlet channel 18, the suction force may no longer be transferred into the interior channel 60 of the tool, and the polyp 2 can become released from the distal end 56. In another example, the suction supply to the working channel 42 can be ceased, and thus the suction within the interior channel 60 will also be ceased, and the polyp 2 can be released. In another example, as the polyp 2 is pulled through the working channel 42, friction between the polyp 2 and the interior surface of the working channel 42 or between the polyp 2 and the distal tip 24 of the endoscope 12 can overcome the vacuum at the shaft distal end 56, which can cause the polyp 2 to become dislodged from the tool 20. After it has been released from the tool 20, the polyp 2 (or any other object that had been captured by the vacuum at the shaft distal end 56) can be removed from the working channel 42 in a conventional manner, such as by suction through the umbilical cable 30 and collected in a trap (not shown) for analysis.

In addition to providing for capture and securing of the tissue sample, as described above, the suction supplied to the shaft distal end 56 of the tool 50 can also be used for other purposes. For example, the suction supplied to the shaft distal end 56 can be used to at least partially deflate the cavity being examined, e.g., after it has been inflated using the air tube 40 of the insertion member 14, or to remove water that has been sprayed into the body cavity by the water tubes 36, 38. The suction supplied to the shaft distal end 56 can also precondition tissue for cutting. For example, the suction can lift up flat tissue, such as a flat polyp, which can make it easier to ensnare and cut the tissue.

Figure 4:
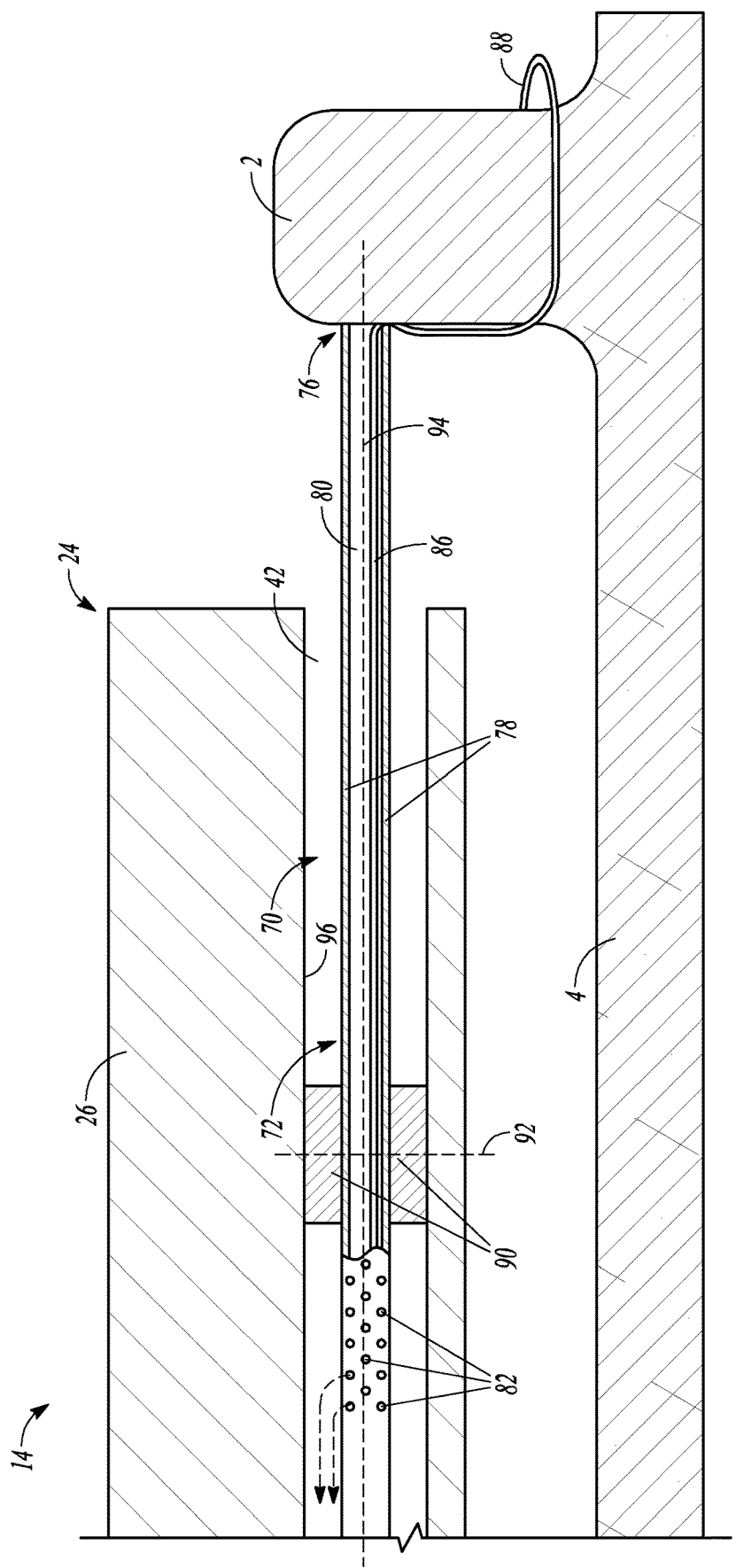
FIG. 4 is a cross-sectional side view of a distal end of a second example tool for use within the example endoscope.

FIG. 4 shows a side view of another example tool 70 that can be used in an endoscope. Like the tool 50 described above with respect to FIG. 3, the tool 70 of FIG. 4 can be used with the endoscope 10 shown in FIG. 1 as the tool 20. In many respects, the tool 70 is similar, if not identical, to tool 50 of FIG. 3. For example, the tool 70 can include an elongated shaft 72 that can extend through the working channel 42 of the endoscope 10. The shaft 72 can extend from a shaft proximal end (e.g., the proximal end 54 of the tool 20 shown in FIG. 1) to a shaft distal end 76. At least a portion of the shaft 72 that is proximal to the shaft distal end 76 can comprise a tubular member 78 with an interior channel 80. The interior channel 80 can extend from the shaft distal end 76 toward the shaft proximal end, for example extending all the way from the shaft distal end 76 to the shaft proximal end. The configuration of the shaft 72, including the tubular member 78 can be similar or identical to those described above with respect to tool 20 (e.g., similar size, cross-sectional shape, etc.).

The tool 70 can be configured to provide for suction-based capture of material, such as a patient's tissue, at the shaft distal end 76. The suction-based capture can be enabled by one or more perforations 82 in the tubular member 78 that extend between the interior channel 80 and an exterior of the elongated shaft 72 of the tool 70. The perforations 82 can provide a fluid pathway between the exterior of the elongated shaft 72 and the interior channel 80, e.g., to provide a fluid pathway between the interior channel 80 and the portion of the working channel 42 surrounding the elongated shaft 72 of the tool 70. The perforations 82 can be configured so that the fluid pathway provided by the perforations 82 can transfer at least a portion of the vacuum from the working channel 42 exterior to the elongated shaft 72 of the tool 70 into the interior channel 80 within the shaft 72. The configuration of the perforations 82 can be similar or identical to those described above with respect to perforations 62 (e.g., similar size or shape of the perforations, similar number of perforations, similar area populated by the perforations, similar perforation density, similar positioning of the perforations relative to the shaft distal end). The tool 70 can also include a cutting or cauterizing structure 86, such as a wire loop 88, similar to that described above.

The primary difference between the tool 70 of FIG. 4 and the tool 50 of FIG. 3 is the inclusion of one or more sealing members 90 coupled to the tubular member 78 that are located between the perforations 82 and the shaft distal end 76. The one or more sealing members 90 and the tubular member 78 can have a larger combined cross-sectional area than the cross-sectional area of the tubular member 78 alone. In an example, "cross-sectional area" can be defined as the area of the one or more sealing members 90 and the tubular member 72 taken along a plane 92 that is normal or substantially normal to a longitudinal axis 94 of the tool 70, as shown in FIG. 4. The lateral dimension of the tubular member 78 (e.g., the diameter for a generally circular cylindrical tubular member 78) and the rest of the elongated shaft 72 can be such that the elongated shaft 72 can be relatively easily inserted through the working channel 42.

The one or more sealing members 90 can provide for increased sealing between the tool 70 and an inner surface 96 of the working channel 42 than the tubular member 78 alone. As used herein, the term "increased sealing" or "increased seal" can refer to an increased resistance to fluid flow past the one or more sealing members 90 compared to fluid flow around the tubular member 78 by itself. The increased resistance to fluid flow can limit the transfer of suction force from the proximal side to the distal side of the one or more sealing members 90, and rather will tend to transfer the suction force through the perforations 82 and into the interior channel 80. The combined cross-sectional area of the one or more sealing members 90 and the tubular member 72 can be configured to correspond to the internal cross-sectional area of the working channel 42 so that the one or more sealing members 90 can provide at least a partial seal against the inner surface 96 of the working channel 42. As shown in FIG. 4, the one or more sealing members 90 can be configured to abut up against the inner surface 96, however this is not required. Similarly, a complete seal, that is a seal that completely prevents movement of fluid across the one or more sealing members 90, may not be required for the one or more sealing members 90, depending on the application and the configurations of the endoscope 10 and the tool 70. Rather, in some examples, the one or more sealing members 90 can be positioned so that there is a close tolerance (e.g., small spacing) between the one or more sealing members 90 and the inner surface 96, so that none or only a portion of the one or more sealing members 90 are actually in contact with the inner surface 96. So long as the one or more sealing members 90 can provide sufficient resistance to fluid flow in order to direct sufficient suction force from the working channel 42 into the interior channel 80 to provide for the desired suction application of the tool 70, such as capture and securing of a tissue sample such as the polyp 2.

The one or more sealing members 90 can be a permanent structure, such as the flange-like one or more sealing members 90 shown in FIG. 4, or it can be a structure that is transformed to form the sealing member. For example, a sealing member can comprise one or more inflatable bladders (not shown) coupled to the outer surface of the tubular member 78. The bladders can start in a deflated configuration to allow for insertion of the shaft 72 into the working channel 42, and then an inflation fluid (e.g., air or water) can be injected into the one or more bladders so that the bladder or bladders can inflate inside the working channel 42 to provide at least a partial seal around the elongated shaft 72.

In an example, the one or more sealing members 90 can be made of a resilient or deformable material that can be partially compressed by the inner surface 96 of the working channel 42 while the elongated shaft 72 is being inserted into the working channel 42. The resilient or deformable material can be capable of at least partially expanding to form at least a partial seal between the one or more sealing members 90 and the inner surface 96.

To better illustrate the endoscope and tool of the present disclosure, a non-limiting list of Examples is provided here:

EXAMPLE 1 can include subject matter (such as an apparatus, a device, a method, or one or more means for performing acts), such as can include a tool for an endoscope. The subject matter can include an elongated shaft including a proximal end and a distal end, wherein the elongated shaft comprises a tubular member with an interior channel extending from the distal end toward the proximal end, and one or more perforations in the tubular member that are spaced from the distal end, the one or more perforations providing fluid communication between an exterior of the elongated shaft and the interior channel.

EXAMPLE 2 can include, or can optionally be combined with, the subject matter of EXAMPLE 1, to optionally include the perforations being configured to transfer suction from the exterior of the elongated shaft into the interior channel.

EXAMPLE 3 can include, or can optionally be combined with, the subject matter of one or any combination of EXAMPLES 1 and 2, to optionally include the transferred suction being sufficient to capture material at the distal end of the elongated shaft.

EXAMPLE 4 can include, or can optionally be combined with, the subject matter of one or any combination of EXAMPLES 1-3, to optionally include the transferred suction being sufficient to capture tissue at the distal end of the elongated shaft.

EXAMPLE 5 can include, or can optionally be combined with, the subject matter of one or any combination of EXAMPLES 1-4, to optionally include one or more sealing members coupled to and extending outwardly from the tubular member.

EXAMPLE 6 can include, or can optionally be combined with, the subject matter of one or any combination of EXAMPLES 1-5, to optionally include the one or more sealing members being located between the one or more perforations and the distal end.

EXAMPLE 7 can include, or can optionally be combined with, the subject matter of one or any combination of EXAMPLES 1-6, to optionally include a combined cross-sectional area of the one or more sealing members and the tubular member being larger than a cross-sectional area of the tubular member alone.

EXAMPLE 8 can include, or can optionally be combined with, the subject matter of one or any combination of EXAMPLES 1-7, to optionally include the one or more sealing members comprising a resilient material.

EXAMPLE 9 can include, or can optionally be combined with the subject matter of one or any combination of EXAMPLES 1-8, to optionally include the one or more sealing members comprising a deformable material.

EXAMPLE 10 can include, or can optionally be combined with, the subject matter of one or any combination of EXAMPLES 1-9, to optionally include the one or more sealing members comprising one or more inflatable bladders.

EXAMPLE 11 can include, or can optionally be combined with, the subject matter of one or any combination of EXAMPLES 1-10, to optionally include a cutting or cauterizing structure.

EXAMPLE 12 can include, or can optionally be combined with, the subject matter of one or any combination of EXAMPLES 1-11, to include subject matter (such as an apparatus, a device, a method, or one or more means for performing acts), such as can include an endoscope, The subject matter can comprise an operating unit comprising one or more controls for operating the endoscope, an insertion member coupled to the operating unit at a proximal end and extending to a distal end, the insertion member comprising a working channel extending from the proximal end to the distal end through an interior of the insertion member, wherein the operating unit is configured to provide suction within the working channel, and a tool insertable through the working channel. The tool can comprise an elongated shaft extendable through the working channel, the elongated shaft comprising a shaft proximal end and a shaft distal end, the elongated shaft comprising a tubular member with an interior channel extending from the shaft distal end toward the shaft proximal end and one or more perforations in the tubular member spaced from the shaft distal end, the one or more perforations providing fluid communication between the working channel of the insertion member and the interior channel of the elongated shaft such that the suction applied to the working channel can be transferred into the interior channel of the tool.

EXAMPLE 13 can include, or can optionally be combined with, the subject matter of one or any combination of EXAMPLES 1-12, to optionally include the one or more perforations being configured such that the suction transferred into the interior channel is sufficient to capture material at the distal end of the elongated shaft.

EXAMPLE 14 can include, or can optionally be combined with, the subject matter of one or any combination of EXAMPLES 1-13, to optionally include the one or more perforations being configured such that the suction transferred into the interior channel is sufficient to capture a tissue sample at the distal end of the elongated shaft.

EXAMPLE 15 can include, or can optionally be combined with, the subject matter of one or any combination of EXAMPLES 1-14, to optionally include the tool further comprising one or more sealing members coupled to and extending outwardly from the tubular member.

EXAMPLE 16 can include, or can optionally be combined with, the subject matter of one or any combination of EXAMPLES 1-15, to optionally include the one or more sealing members being located between the one or more perforations and the shaft distal end.

EXAMPLE 17 can include, or can optionally be combined with, the subject matter of one or any combination of EXAMPLES 1-16, to optionally include a combined cross-sectional area of the one or more sealing members and the tubular member being larger than a cross-sectional area of the tubular member alone.

EXAMPLE 18 can include, or can optionally be combined with, the subject matter of one or any combination of EXAMPLES 1-17, to optionally include the one or more sealing members comprising a resilient material.

EXAMPLE 19 can include, or can optionally be combined with, the subject matter of one or any combination of EXAMPLES 1-18, to optionally include the one or more sealing members comprising a deformable material.

EXAMPLE 20 can include, or can optionally be combined with, the subject matter of one or any combination of EXAMPLES 1-19, to optionally include the one or more sealing members comprising one or more inflatable bladders.

EXAMPLE 21 can include, or can optionally be combined with, the subject matter of one or any combination of EXAMPLES 1-20, to optionally include the one or more sealing members providing an increased resistance to movement of fluid across the one or more sealing members compared with the tubular member alone.

EXAMPLE 22 can include, or can optionally be combined with, the subject matter of one or any combination of EXAMPLES 1-21, to optionally include the tool being extendable by a first distance from the distal end of the insertion member.

EXAMPLE 23 can include, or can optionally be combined with, the subject matter of one or any combination of EXAMPLES 1-22, to optionally include the one or more perforations being spaced from the shaft distal end by a second distance that is greater than or equal to the first distance.

EXAMPLE 24 can include, or can optionally be combined with, the subject matter of one or any combination of EXAMPLES 1-23, to optionally include a cutting or cauterizing structure.

EXAMPLE 25 can include, or can optionally be combined with, the subject matter of one or any combination of EXAMPLES 1-24, to optionally include the use of a single suction source for supplying suction to the working channel and to the interior channel of the tool.

The above Detailed Description is intended to be illustrative, and not restrictive. For example, the above-described examples (or one or more elements thereof) can be used in combination with each other. Other embodiments can be used, such as by a person of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Although the invention has been described with reference to exemplary embodiments, workers skilled in the art will recognize that changes may be made in form and detail without departing from the spirit and scope of the invention.

What is claimed is:

1. A cutting and resection tool for use with an endoscope that is insertable into a body cavity of a patient to examine the body cavity and to cut and resect a polyp from the body cavity, the endoscope comprising a working channel, wherein suction is applied to the working channel from a suction source through an umbilical cable, the cutting and resecting tool comprising:

a cutting structure configured to cut and resect the polyp from the body cavity; an elongated, flexible shaft configured to be inserted completely through the working channel of the endoscope during an exploratory procedure through a tool inlet channel that is separate from the umbilical cable, the elongated shaft including a proximal end and a distal end, wherein the elongated shaft comprises a tubular member with an interior channel extending from the distal end toward the proximal end, wherein the tubular member is configured to be extended distally from a distal tip of the endoscope, and wherein the distal end of the elongated shaft is configured to be put in contact with the polyp when the tubular member is extended distally from the distal tip; and one or more perforations in the tubular member that are spaced from the distal end, the one or more perforations providing fluid communication between the exterior of the elongated shaft and the interior channel, wherein the one or more perforations are configured to transfer at least a portion of the suction from the working channel around the exterior of the elongated shaft into the interior channel;

wherein the transferred suction creates a vacuum at the distal end, wherein the distal end is configured so that the vacuum produces a vacuum force that is exerted between the distal end and the polyp when the distal end is in contact with the polyp;

wherein the one or more perforations, the tubular member, and the distal end are configured so that the portion of the suction transferred into the interior channel is sufficient so that the vacuum force at the distal end secures the polyp to the distal end of the elongated shaft, during cutting and resection of the polyp and is sufficient such that the vacuum force at the distal end holds the resected polyp at the distal end after the polyp has been cut and resected from the body cavity; and wherein the elongated shaft is configured to be proximally withdrawn through the working channel while maintaining the vacuum force through the one or more perforations while the one or more perforations are within the working channel, and wherein the one or more perforations and the elongated shaft are configured so that when the suction is applied to the working channel, the portion of the suction transferred into the interior channel is sufficient so that the vacuum force continues to hold the resected polyp at the distal end while the elongated shaft is proximally withdrawn through the working channel.

2. The cutting and resecting tool of claim 1, further comprising one or more sealing members coupled to the tubular member, the one or more sealing members being located between the one or more perforations and the distal end.

3. The cutting and resecting tool of claim 2, wherein a combined cross-sectional area of the one or more sealing members and the tubular member is larger than a cross-sectional area of the tubular member alone.

4. The cutting and resecting tool of claim 2, wherein the one or more sealing members comprise at least one of:
a resilient or deformable material, or one or more inflatable bladders.

5. The cutting and resecting tool of claim 1, wherein the cutting structure is further configured to cauterize the body cavity.

6. The cutting and resecting tool of claim 1, wherein one or more characteristics of the one or more perforations are selected to provide for the portion of the suction transferred into the interior channel that, is sufficient, so that the vacuum, force secures the polyp to the distal end of the elongated shaft during the cutting and resection of the polyp and holds the resected polyp at the distal end after the polyp has been cut and resected from the body cavity, the one or more characteristics comprising at least one of a number of perforations in the tubular member; size or sizes of the one or more perforations; shape or shapes of the one or more perforations; pattern of the one or more perforations on the tubular member; overall, area of the tubular member populated by the one or more perforations; and packing or density of the one or more perforations on the tubular member.

7. The cutting and resecting tool of claim 1, wherein the suction source is the only source for supplying suction to the tool.

8. The cutting and resecting tool of claim 1, wherein the cutting and resecting tool is structured for use with a colonoscope.

9. An endoscope comprising:
an operating unit comprising one or more controls for operating the endoscope;
a flexible insertion member configured to be inserted into a body cavity of a patient, wherein the body cavity is proximate to a tissue structure of the patient, the insertion, member being coupled to the operating unit at an insertion-member proximal end and extending to an insertion-member distal end, the insertion member comprising a working channel extending from the insertion-member proximal end to the insertion-member distal end through an interior of the insertion member;
an umbilical cable coupled to the operating unit, wherein the umbilical cable is in fluid communication with the working channel;
a suction source in fluid communication with the operating unit via the umbilical cable, wherein the suction source provides suction to the working channel via the umbilical cable;
a tool inlet channel through the operating unit that connects with the working channel, wherein the tool inlet channel is separate from the umbilical cable;
a cutting structure configured to cut and resect a tissue polyp from the tissue structure; and
a tissue-securing tool comprising:
an elongated shaft configured to be inserted through the tool inlet channel and completely through the working channel during an exploratory procedure, the elongated shaft comprising a shaft proximal end and a shaft distal end, the elongated shaft comprising a tubular member with an interior channel extending from the shaft distal end toward the shaft proximal end, wherein the tubular member is configured to be extended distally from the insertion-member distal end and the shaft distal end is configured to be put into contact with the tissue polyp when the tubular member is extended distally from the insertion-member distal end; and
one or more perforations in the tubular member spaced from the shaft distal end, the one or more perforations providing fluid communication between the working channel exterior to the elongated shaft and the interior channel, wherein the one or more perforations are configured to transfer at least a portion of the suction from the working channel exterior to the elongated shaft into the interior channel of the elongated shaft;
wherein the transferred suction creates a vacuum at the shaft distal end, wherein the shaft distal end is configured so that the vacuum produces a vacuum force that is exerted between the shaft distal end and the tissue polyp when the distal end is in contact with the tissue polyp;
wherein the one or more perforations, the tubular member, and the shaft distal end are configured so that when the suction is applied to the working channel, the portion of the suction transferred into the interior channel is sufficient so that the vacuum force at the shaft distal end secures the tissue polyp to the shaft distal end during cutting and resecting of the tissue polyp from the tissue structure with the cutting structure and holds the resected tissue polyp at the shaft distal end after the tissue polyp has been cut and resected from the tissue structure; and
wherein the elongated shaft is configured to be proximally withdrawn through the working channel while maintaining the vacuum force through the one or more perforations while the one or more perforations are within the working channel, and wherein the one or more perforations and the elongated shaft are configured so that when the suction is applied to the working channel, the portion of the suction transferred into the interior channel is sufficient so that the vacuum force continues to hold the resected tissue polyp at the distal end while the elongated shaft is proximally withdrawn through the working channel.

10. The endoscope device of claim 9, wherein the tissue-securing tool further comprises one or more sealing members coupled to the tubular member, the one or more sealing members being located between the one or more perforations and the shaft distal end.

11. The endoscope device of claim 10, wherein a combined cross-sectional area of the one or more sealing members and the tubular member is larger than a cross-sectional area of the tubular member alone.

12. The endoscope device of claim 10, wherein the one or more sealing members comprise at least one of a resilient or deformable material or one or more inflatable bladders.

13. The endoscope device of claim 10, wherein the one or more sealing members provide an increased resistance to movement of fluid across the one or more sealing members compared with the tubular member alone.

14. The endoscope of claim 9, wherein the elongated shaft of the tissue-securing tool is configured to extend it from the insertion-member distal end by a first distance so that the shaft distal end can be put into contact with the tissue polyp, and wherein each of the one or more perforations are spaced from the shaft distal end by at least a second distance, wherein the second distance is greater than or equal to the first distance.

15. The endoscope of claim 9, wherein the cutting structure is configured to cut and resect the tissue polyp from the tissue structure and to cauterize the tissue structure.

16. The endoscope of claim 9, wherein the working-channel suction source is the only suction source supplying suction to the endoscope.

17. The endoscope of claim 9, wherein the tissue polyp to be resected is a colon polyp.

18. The endoscope of claim 9, wherein the elongated shaft of the tissue-securing tool is configured to be proximally withdrawn through the working channel, and wherein the one or more perforations and the elongated shaft are configured so that when the suction is applied to the working channel, the portion of the suction transferred into the interior channel is sufficient so that the vacuum force continues to hold the resected tissue polyp at the shaft distal end while the elongated shaft is proximally withdrawn through the working channel to provide for removal and recovery of the resected tissue polyp through the working channel.

19. The endoscope of claim 9, further comprising a trap configured to collect or receive the resected tissue polyp.

20. The cutting and resecting tool of claim 9, wherein one or more characteristics of the one or more perforations are selected to provide for the portion of the suction transferred into the interior channel that is sufficient so that the vacuum force secures the tissue polyp to the shaft distal end during the cutting and resection of the tissue polyp and holds the resected tissue polyp at the shaft distal end after the tissue polyp has been cut and resected from the tissue structure, the one or more characteristics comprising at least one of a number of perforations in the tubular member; size or sizes of the one or more perforations; shape or shapes of the one or more perforations; pattern of the one or more perforations on the tubular member; overall area of the tubular member populated by the one or more perforations; and packing or density of the one or more perforations on the tubular member.

21. The endoscope of claim 9, wherein the endoscope is a colonoscope.

* * * * *